United States Patent [19]
Sterling et al.

[11] Patent Number: 5,348,146
[45] Date of Patent: Sep. 20, 1994

[54] SUTURE PACKAGE

[75] Inventors: Michael Sterling, Danbury; Susan Critzer, Brookfield, both of Conn.

[73] Assignee: American Cyanamid Co., Wayne, N.J.

[21] Appl. No.: 16,363

[22] Filed: Feb. 11, 1993

[51] Int. Cl.$^5$ .............................................. A61L 17/02
[52] U.S. Cl. ..................... 206/63.3; 206/492
[58] Field of Search .................. 206/63.3, 63.5, 380, 206/382, 339, 338, 492

[56] References Cited

U.S. PATENT DOCUMENTS

| | | |
|---|---|---|
| 3,136,418 | 6/1964 | Stacy et al. . |
| 3,162,307 | 12/1964 | Regan, Jr. . |
| 3,363,751 | 1/1968 | Shave et al. . |
| 3,857,484 | 12/1974 | Thyen .......................... 206/63.3 X |
| 4,014,434 | 3/1977 | Thyen . |
| 4,121,711 | 10/1978 | Bolanowski ...................... 206/63.3 |
| 4,142,628 | 3/1979 | Marocco et al. .................. 206/63.3 |
| 4,491,218 | 1/1985 | Aday . |
| 4,496,045 | 1/1985 | Ferguson et al. . |
| 4,574,948 | 3/1986 | Huck et al. . |
| 4,574,957 | 3/1986 | Stead . |
| 4,708,241 | 11/1987 | Black . |
| 4,884,681 | 12/1989 | Roshdy et al. . |
| 5,048,678 | 10/1991 | Chambers . |
| 5,076,431 | 12/1991 | Thompson . |
| 5,086,914 | 2/1992 | Mish et al. . |

FOREIGN PATENT DOCUMENTS 2332359  11/1975  France .

*Primary Examiner*—Jacob K. Ackun, Jr.
*Attorney, Agent, or Firm*—Charles F. Costello, Jr.

[57] ABSTRACT

A direct dispensing, surgical suture package is disclosed. The package comprises a first rectangular panel 1 and a second rectangular panel 2. The second panel is foldably connected to a short side of the first rectangular panel. The package also comprises a first rectangular flap 3 which is foldably connected to a long side of the first rectangular panel. Further, the package comprises a second rectangular flap 4. The second flap is foldably connected to a long side of the second rectangular panel. The package further comprises means for accessing a surgical needle between the second rectangular panel and flap. The package is useful for dispensing a suture from it without having to open, tear or mutilate any of the panels or flaps.

1 Claim, 4 Drawing Sheets

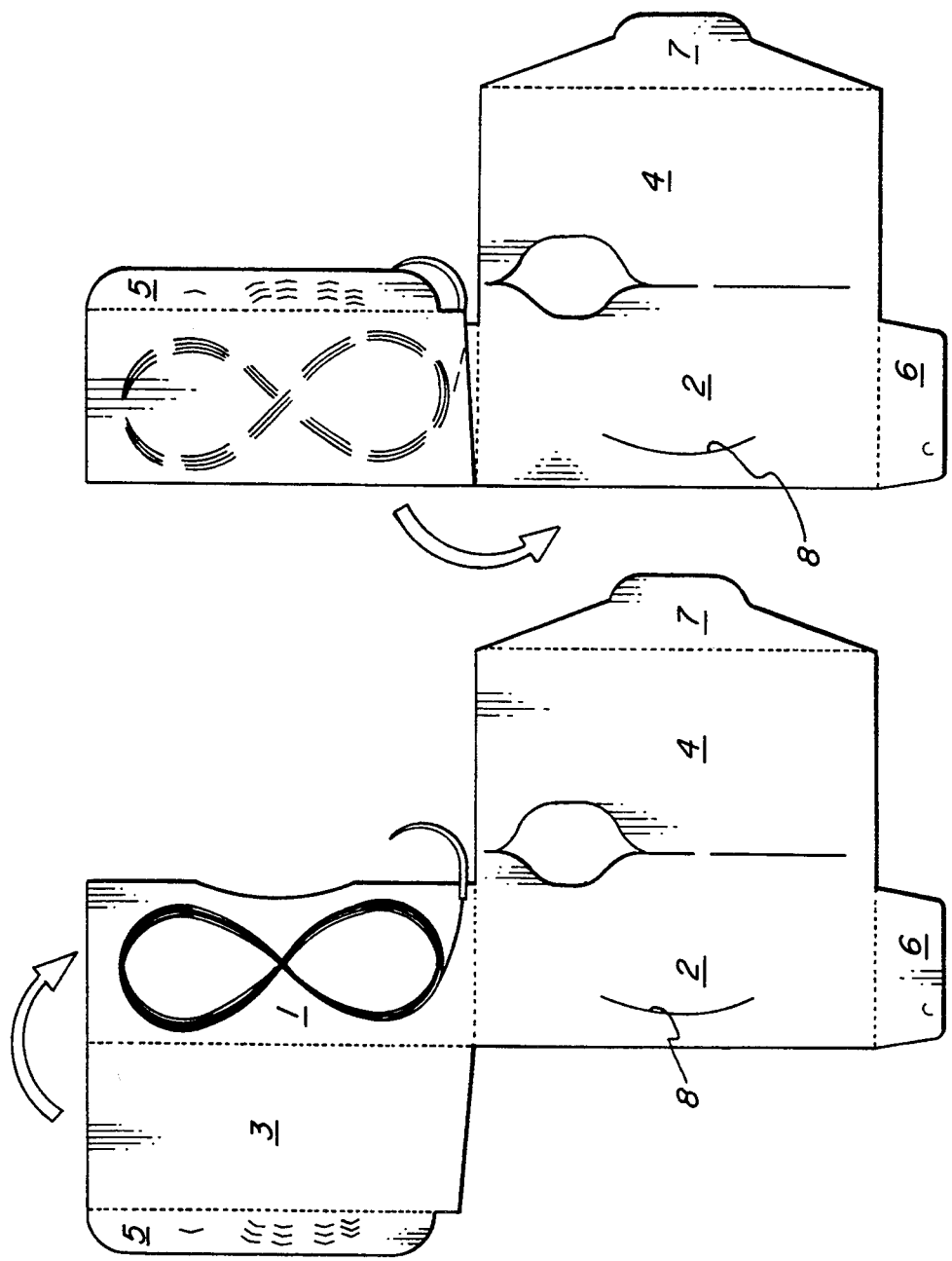

SUTURE PACKAGE

BACKGROUND AND SUMMARY OF THE INVENTION

This invention relates to a surgical suture package. The package is self-contained and permits dispensing of a single-armed or double-armed suture, with or without a pledget.

The significance of packaging is most evident in the packaging of surgical sutures. It is essential that the package protect the product and maintain sterility throughout its period of potential use. Sutures may be stored in hospitals for several years, although the usual storage time is much shorter. It is also essential that the package provide rapid and positive means of identification, and release of the undamaged product, ready for use by the surgeon.

There are many sizes of sutures, and many materials of construction such as catgut or polyglycolic acid for absorbables, and silk, cotton, nylon, polyethylene terephthalate, polypropylene, stainless steel, insulated stainless steel and other materials for use as non-absorbables. There are several different needle types in common use including pointed straight, pointed curved, three cornered straight, three cornered curved, curved both regular and reverse cutting, and needles with side cutting edges of various types. The variations and combinations of each of the above, to meet the preferences of many surgeons for different operative procedures, means that the suture manufacturer needs to supply different suture package combinations. These suture package combinations can run into the thousands. The importance of positive identification while maintaining an efficient, economical package can thus be readily appreciated.

It is also important to provide convenience to the surgeon and to limit the risk of accidentally enclosing foreign items in the patient by limiting the number of extraneous packaging materials associated with use of the product in the operating theater. A count is often kept to ensure that each item is accounted for and removed from the operating field. Considering the ramifications of accidentally enclosing such material in the patient during the surgical procedure, is it absolutely essential to minimize this hazard.

Finally, it is essential in a package containing a surgical needle or needles, that the suture is protected from contact with the sharp point or cutting edge of the needle, which could partially cut the suture or the package. Also, the armed needle edges and point need to be protected to maintain their sharpness.

The prior art generally discloses a surgical suture or sutures package in a outer envelope. Contained in the outer envelope is an inner envelope or pouch which is sterile. The suture strand or strands have been formed into various configurations of coils and loops, and are contained in or on various retainers, cards, or reels within the inner envelope.

The suture is normally prepared for the surgeon by peeling open the outer envelope and transferring the inner envelope by sterile forceps, or by projecting it across a sterile barrier, into the sterile area of the operating room. The sterile inner envelope is then opened at the time of use.

The package of the present invention has advantages over the prior art. After peeling open the outer envelope, the card containing the suture is exposed. The suture can then be dispensed without opening the card, either from the front (for right-handed arming), or the back (for left-handed arming). The needle is completely visible, as is its point orientation.

Another advantage is that the self-contained suture card can be printed with complete suture and needle identification. Special ink effects, e.g. striping and coloring used in the printing, allows a color coding description of the suture and/or needle materials for ease of identification.

The surgical suture card described is enclosed in an envelope. At least one web of the envelope is a clear (transparent) material which allows full visibility of the descriptive literature on the card. The envelope is sealed by methods known in the art, e.g. heat sealing.

An improved surgical suture package containing a single surgical suture strand (single- or double-armed, with or without a pledget) has been invented. The package comprises a paper or similar material card with four main rectangular panels, such that when folded in a prescribed manner, a suture compartment is created into which the suture may be manually or automatically wound.

The label is divided with perforations or scores into four main panels. Two of these panels 1, 2 are joined at one of the narrower ends. To one of these is connected a third panel 3 along the longer edge. To the other panel is connected a fourth panel 4 along the opposite longer edge. Along the joining edge of these two panels is an opening, either symmetric or asymmetric to the joining edge.

In addition to the main panels, there are three lesser flaps, each connected to a different panel. A flap with slits 5, designed for retaining the various surgical needles, is connected to the third panel on the available longer side. To the shorter edge of the second panel is attached a lesser flap 6 which completes the suture compartment when folded. To the longer edge of the fourth panel is connected a tab 7 which may be tucked into a slit in the second panel upon completion of folding.

Upon complete folding, the aforementioned opening creates a recess, through which the needled suture may be directly accessed without opening any flaps or tabs.

Further, an improvement may be made in which a foam block may be adhered with adhesive on the flap with slits 5 for embedding the needle for tip protection.

DESCRIPTION OF THE DRAWINGS

FIG. 1 is a front view of the support card;

FIG. 2 is a front view showing the preferred folding sequence of the left-hand flap 3 onto the main panel 1 forming the suture compartment;

FIG. 10 also shows the preferred orientation of the suture support card before loading it into a envelope having at least one transparent side.

DETAILED DESCRIPTION

The following embodiments describe the best mode of carrying out the invention.

Figure 8:
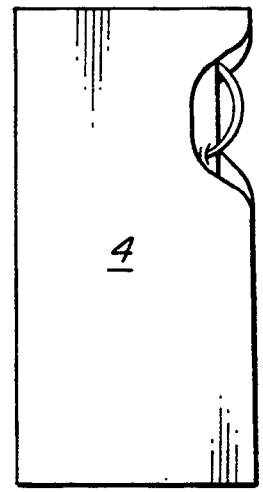
FIG. 8 is a front view of the preferred folding sequence of the tuck tab 7 behind the suture support card self-containing the suture package.

Referring to FIG. 8, the suture support card is and remains before, during and after its use a single piece. The needled suture end is exposed at all times ready for dispensing without moving any flaps or tabs, from the front or back. The needled strand end can be lifted with the hand or with a needle holder.

The card is preferably manufactured from a sterilizable paper of about 90 lb. weight, capable of withstanding sterilization without adverse effects. The paper may be coated with about ½ mil polyethylene so it is heat sealable. Such paper is known in the trade and is readily available.

The self contained suture support card of this invention may be used with a outer envelope. The envelope material, the method of manufacturing the envelope, and the method of loading the self-contained card of FIG. 9 into the envelope are well-known in the suture packaging art.

After the suture is dispensed, the card continues to be intact and in one piece. Thus no additional materials or articles other than the surgical suture are added to the operating area. Related hazards are thus minimized and accountability is simplified.

Figure 9:
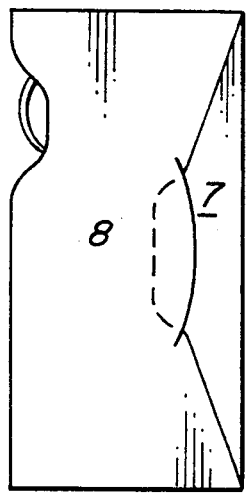
FIG. 9 is a back view showing the insertion of tuck tab 7 into a receptacle slit for completing the fold on the support card.
Figure 10:
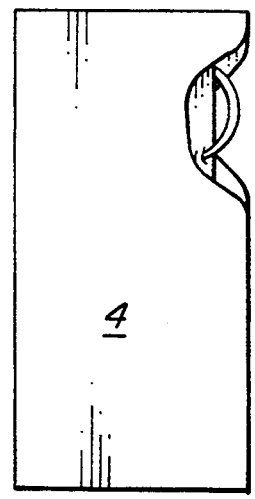
FIG. 10 is a front view showing the completely folded support card holding the needled suture as presented to a right-handed surgeon during use.
Figure 11:
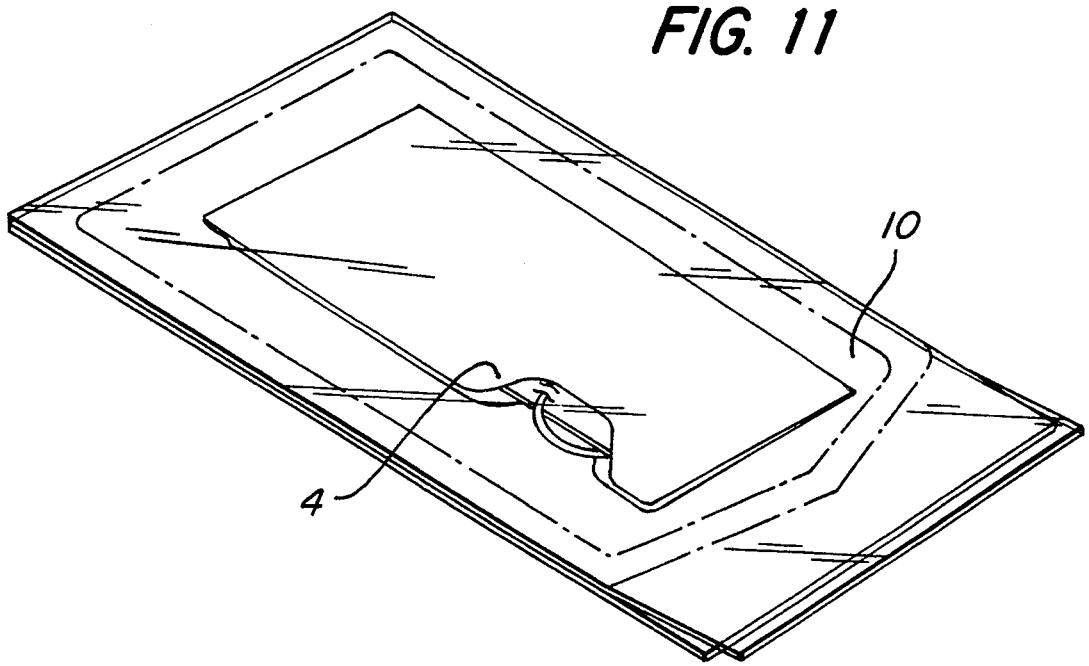
FIG. 11 is a perspective view showing the preferred loading of the suture package of FIG. 10, with the flap 4 visible, into a peelable envelope 10.

FIG. 1 shows a preferred suture card. The card is cut out and scored from a sheet of sterilizable paper, which may be coated with polyethylene for heat sealing by a method known in the art. The card consists of two central panels 1,2 to each of which are foldably attached a first and second side flap 3,4 to opposite edges. To central panel 2 is foldably attached a lesser flap 6. To flap 3 is foldably attached a lesser flap 5 containing slits for needle retention. To flap 4 is foldably attached a lesser locking tab 7. The tab 7 is placed into the retaining slit 8 on central panel 2, as shown in FIG. 9, and after the folding sequence shown in FIGS. 2–7.

Figure 5:
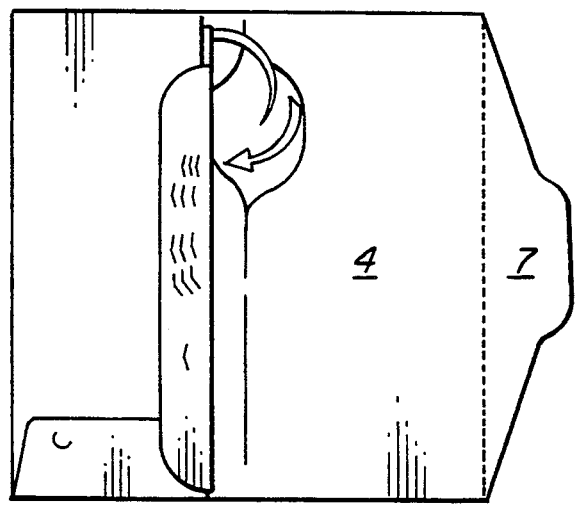
FIG. 5 is a front view of the preferred folding sequence of the needle flap 5 onto the suture compartment, thereby fully enclosing the suture within.
Figure 6:
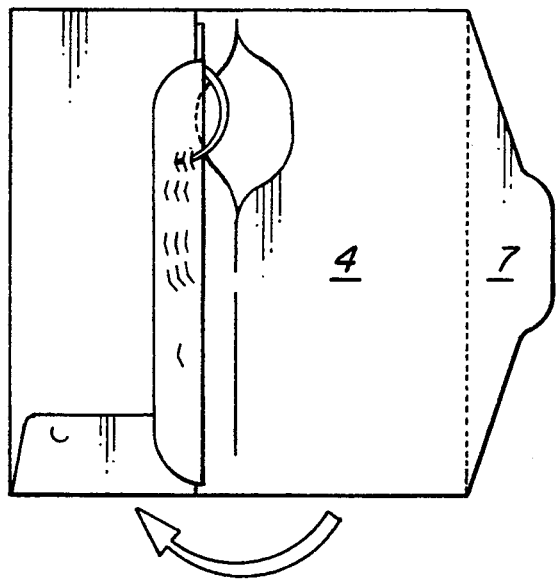
FIG. 6 is a front view showing the placement of the needle in the slits of the needle flap 5 according to design and the size of the needle.
Figure 7:
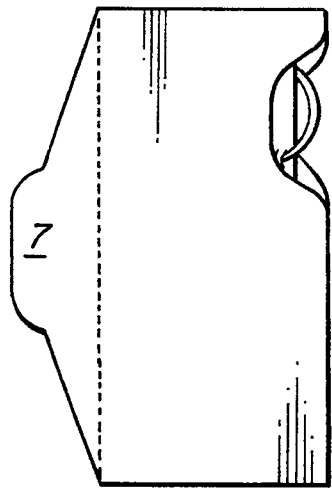
FIG. 7 is a front view of the preferred folding sequence of the flap 4 onto the fully enclosed suture compartment.

Referring to FIG. 5, for a curved needle, the desired orientation is usually such that the arc of travel from the butt to the point is in a clockwise direction. This orientation is sometimes termed a right-handed orientation because on dispensing, the needle is properly presented for a right-handed use. The needles are thus placed into the needle slits on flap 5 with a right-handed orientation. Since this package can be used from either the front (for a right-handed user) or the back (for a left-handed user), either needle orientation may be accessed, depending on the "handedness" of the user, which is a significant advantage.

Figure 3:
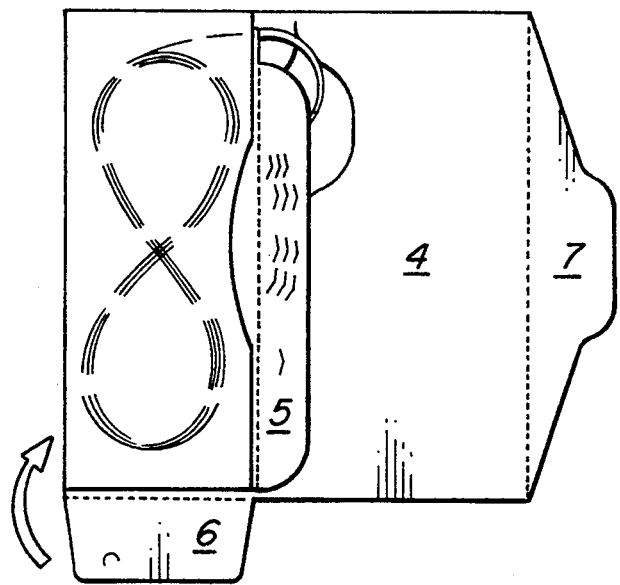
FIG. 3 is a front view showing the preferred folding sequence of the flap 3 and panel 1 onto panel 2 further forming the suture compartment.
Figure 4:
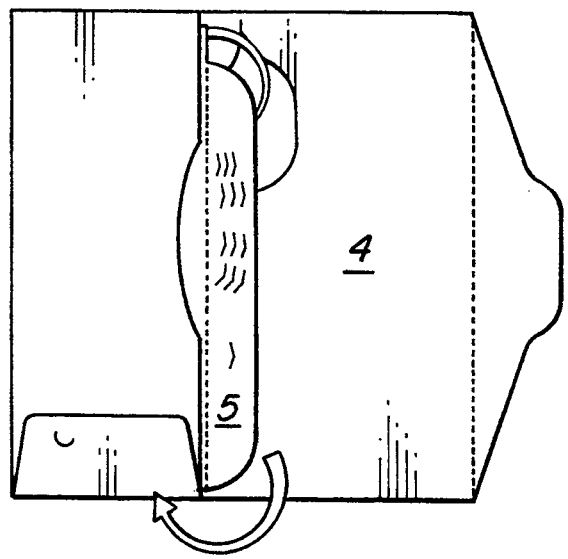
FIG. 4 is a front view showing the preferred folding sequence of the lesser flap 4 further enclosing the suture compartment.

FIGS. 2–8 show the preferred folding and self-containing of the suture support card. Specifically, FIG. 2 shows a flap 3 folding onto the panel 1 enclosing the suture. The suture matrix can be achieved by winding by hand in a figure 8 or serpentine configuration, or by machine yielding the same result, so that when dispensed, the suture is freely removed from the package and ready for use. FIG. 3 shows the folding of the suture compartment 1,3 onto panel 2.

Referring specifically to FIGS. 4 to 7, the folding sequence is illustrated in relation to enclosing the suture compartment with lesser flaps 5,6, and placing the needle in the slits of flap 5.

FIG. 8 shows a means for self-containing the support card. That is, a tab lock 7 is inserted into the slit of panel 2 to provide a self-contained package.

What is claimed is:

1. A two part, self-contained package, the package having a first part capable of dispensing a sterile surgical suture, the first part comprising:
   a first rectangular panel 1;
   a second rectangular panel 2 foldably connected at a short side thereof to a short side of the first rectangular panel, the second panel containing a first slit;
   a first rectangular flap 3 foldably connected to a long side of said first rectangular panel;
   a second rectangular flap 4 foldably connected to a long side of the second rectangular panel;
   a third flap 5 foldably connected to a long side of the first rectangular flap, the third flap containing a plurality of second slits for retaining a surgical needle;
   a fourth flap 7 foldably connected to a long side of the second rectangular flap;
   a tuck tab 8 foldably connected to the other short side of said second rectangular panel; and
   a recess between said second rectangular panel and said second rectangular flap, for accessing a surgical needle;
   and a second part comprising:
   an envelope capable of being peeled opened, said first part contained within said envelope.

* * * * *